United States Patent [19]
Kimura et al.

[11] Patent Number: 5,499,545
[45] Date of Patent: Mar. 19, 1996

[54] PIPETTING DEVICE AND METHOD THEREFORE

[75] Inventors: Akira Kimura, Tokyo; Tadashi Watanabe; Tsuyoshi Inoue, both of Kanagawa; Keiichi Nakamachi, Saitama, all of Japan

[73] Assignee: Sony Corporation, Tokyo, Japan

[21] Appl. No.: 261,117

[22] Filed: Jun. 14, 1994

[30] Foreign Application Priority Data

Jun. 18, 1993 [JP] Japan .................... 5-170925

[51] Int. Cl.$^6$ .............. G01F 11/06; B01L 3/02
[52] U.S. Cl. .................. 73/864.18; 73/863.01; 73/864.14; 222/55
[58] Field of Search .............. 73/864.18, 864.16, 73/863.01, 863.02, 863.03, 864.13, 864.14, 864.17; 222/55; 422/100

[56] References Cited

U.S. PATENT DOCUMENTS

| | | | |
|---|---|---|---|
| 3,591,056 | 7/1971 | Griffin ........................... | 73/864.18 |
| 4,675,130 | 6/1987 | Charneski et al. ............. | 73/863.01 X |
| 4,777,832 | 10/1988 | Prodosmo et al. ........... | 73/863.02 |
| 4,794,085 | 12/1988 | Jessup et al. .................. | 73/863.01 X |
| 5,013,529 | 5/1991 | Itoh ................................ | 73/863.01 X |
| 5,143,819 | 9/1992 | Barry et al. .................... | 73/863.01 X |
| 5,158,748 | 10/1992 | Obi et al. ....................... | 73/863.01 X |
| 5,380,486 | 1/1995 | Anami ............................ | 73/863.01 X |

Primary Examiner—Thomas P. Noland
Attorney, Agent, or Firm—Ronald P. Kananen

[57] ABSTRACT

Measurement accuracy is improved by eliminating the influence of changes in the atmospheric and internal pressures on the quantity of a liquid absorbed or discharged. A pipetting device inducts a specified quantity of liquid into a tip portion or discharges a specified quantity of liquid from the tip portion by controlling the pressure inside a cylinder portion including a cylinder and a piston. A control target value for the quantity of the liquid to be absorbed or discharged from a command portion and information from an atmospheric pressure measurement portion and a pressure sensor for detecting the internal pressure of the cylinder are sent to a correction calculation portion which in turn performs correction calculation based on measured data on the atmospheric and internal pressures and data on the shapes of the cylinder and tip portion to obtain the distance to be traveled by the piston so that the control target value form the command portion is met. A control portion controls a motor which drives the piston in accordance with information on the distance to be traveled by the piston from the correction calculation portion.

9 Claims, 8 Drawing Sheets

10 ··· TIP PORTION
11 ··· CYLINDER
12 ··· PISTON
17 ··· PRESSURE MEASUREMENT PORTION

10 ··· TIP PORTION
10B, 10M, 10T ··· PORTION
11 ··· CYLINDER
12 ··· PISTON

10 ··· TIP PORTION

10 ··· TIP PORTION

10 ⋯ TIP PORTION

1

PIPETTING DEVICE AND METHOD THEREFORE

BACKGROUND OF THE INVENTION

1. Field of the Invention

The present invention relates to a novel pipetting device for inducting and discharging a liquid. More particularly, the present invention provides a novel pipetting device and method for inducting and discharging a liquid which inducts a liquid into a tip portion thereof in a specified quantity and discharges the inducted liquid from the tip portion in a predetermined quantity by way of pressure control which is corrected in response to changes in the internal pressure of the tip portion and fluctuations in the atmospheric pressure.

2. Description of the Related Art

Devices for inducting a liquid contained in a container in a specified quantity and then transferring the inducted liquid to another container are referred to as pipetting devices.

Such a pipetting device has a configuration wherein a piper portion is provided at a tip portion thereof. The tubular tip portion is dipped in liquid in a container and a negative pressure is produced in the tip portion to induct a liquid. Thereafter, the liquid in the tip portion is discharged by pressurizing the tip portion after it is moved to another container.

Such a conventional device however, suffers from the drawback that there is variation in metering accuracy due to changes in the internal pressure of the tip portion as a result of the induction of liquid and fluctuations in the atmospheric pressure which hinders stable induction of the liquid.

In other words, the internal pressure of the tip portion changes when a liquid is inducted into or discharged from the tip portion. As a result, if the volume inside the tip portion is large and a large quantity of liquid is inducted, there will be an error which is large relative to the specified quantity. The only way to reduce such an error has been to reduce the volume inside the tip portion as much as possible.

Further, the measurement error depends on the weather at the time of the measurement and, for example, an error becomes larger when a depression passes.

SUMMARY OF THE INVENTION

In order to solve the above-described problem, the present invention provides a liquid inducting and discharging device for inducting or discharging a specified quantity of liquid by controlling the pressure in a cylinder-like portion including a piston and a cylinder, comprising a command portion for specifying a control target value for the quantity of liquid to be inducted or discharged, a pressure measurement portion for measuring the atmospheric pressure and/or the internal pressure of the cylinder, a correction calculation portion for obtaining the distance to be traveled by the piston by making a calculation to correct the control target value from the command portion based on measured data from the pressure measurement portion and data for the shape of a tip portion of the cylinder-like portion, and a control portion for controlling a piston driving means according to the information from the correction calculation portion relating to the distance to be traveled by the piston.

The liquid inducting and discharging device according to the present invention is a pipetting device which inducts or discharges a specified quantity of liquid by controlling the pressure in a cylinder-like portion which includes a piston and a cylinder. The atmospheric pressure and/or the internal pressure of the cylinder is measured after the control target value for the quantity of liquid to be inducted or discharged is specified; the distance to be traveled by the piston is derived by correcting the control target value based on the measured atmospheric pressure and/or the internal pressure of the cylinder and data relating to the shape of a tip portion of the cylinder-like portion. The piston displacement is controlled so that the distance traveled by the piston meets the value obtained using the correction calculation.

According to the present invention, a calculation is made based on measured data indicative of the atmospheric pressure and/or the internal pressure of the piston and data pertaining to the shape of the cylinder, to correct the control target value of the quantity of liquid to be inducted or discharged. The distance to be traveled by the piston is obtained taking changes in the pressures into consideration. As a result, the piston displacement can be controlled in response to fluctuation in the atmospheric pressure and changes in the internal pressure of the tip portion to improve accuracy in measuring the quantity of liquid.

DETAILED DESCRIPTION OF THE EMBODIMENT

The device and method for inducting and discharging a liquid according to the present invention will now be described with reference to the illustrated embodiment.

Figure 1:
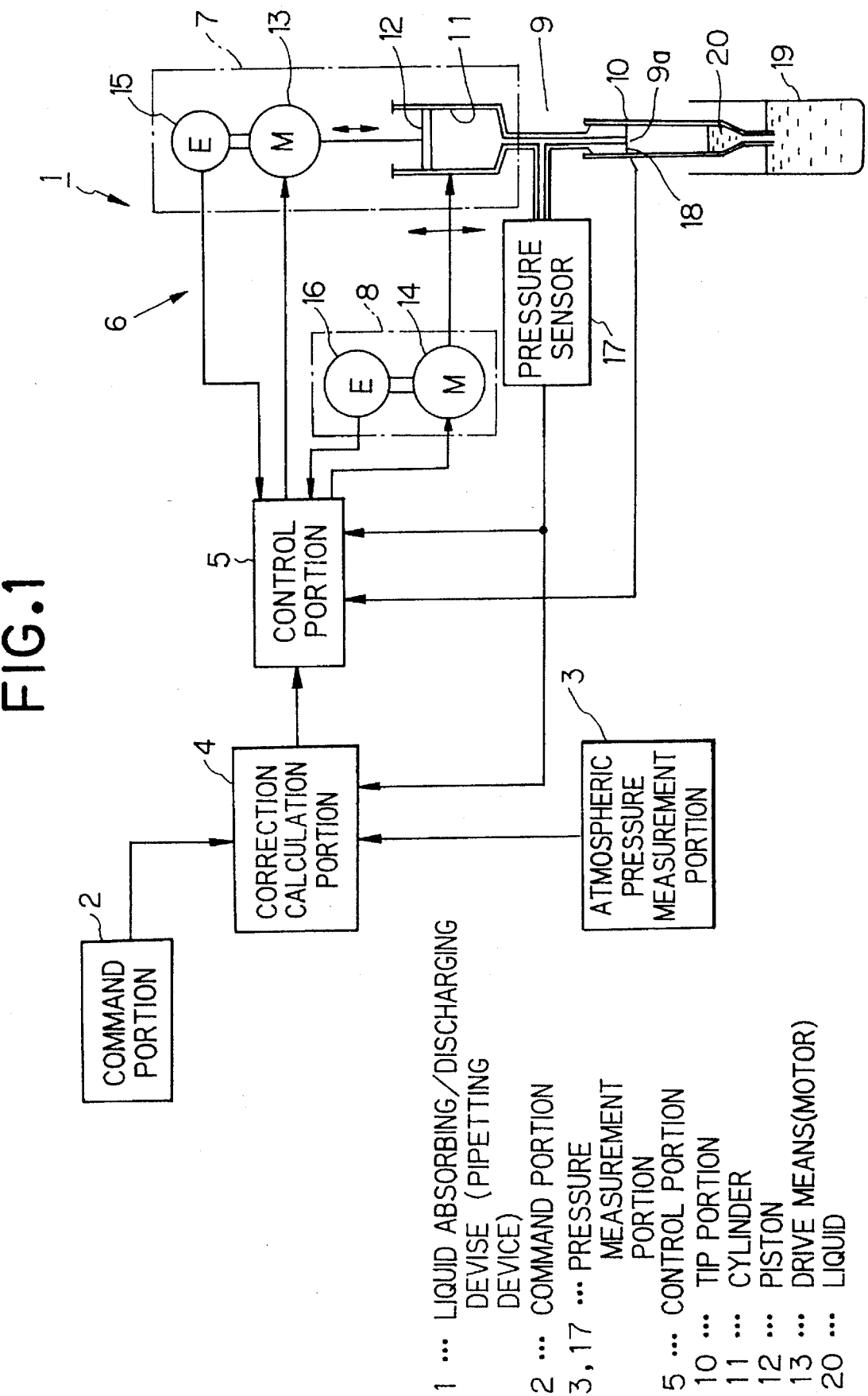
FIG. 1 schematically illustrates a pipetting device according to the present invention.

FIG. 1 shows the structure of a pipetting device 1 according to the present invention in a manner which demonstrates its operational principles.

The pipetting device 1 comprises a command section or portion 2, an atmospheric pressure measurement section or portion 3, a correction calculation section or portion 4, a control section or portion 5, and a controlled section or portion 6.

The command portion 2 sets a control target value indicative of the amount of iquid which is required to be inducted and/or discharged, and which is sent to the correction calculation portion 4.

The atmospheric pressure measurement portion 3 measures the atmospheric pressure and sends information indicative of fluctuations in the atmospheric pressure to the correction calculation portion 4.

The correction calculation portion 4 receives the control target value from the command portion 2 and the information from the atmospheric pressure measurement portion 3, corrects a control value, and sends the result of the correction to the control portion 5. A memory portion in the correction calculation portion 4 stores various kinds of data (e.g. data relating to the shape of a cylinder and a tip portion) required for calculation formulas which will be described later.

The control portion 5 is responsible for controlling a pressurization/pressure reduction control portion 7 and a movement control portion 8 which form the controlled portion 6, in accordance with commands from the correction calculation portion 4.

Reference numeral 9 designates a piper portion of the pipetting device 1. A tubular tip portion 10 is detachably mounted on the lower end of this device.

The piper portion 9 is formed with a communicating bore 9a which is in communication with the tip portion 10, and which is also connected to the pressurization/pressure reduction control portion 7.

The pressurization/pressure reduction control portion 7 in this arrangement comprises, for example, a mechanism which as illustrated has a cylinder 11 and a piston 12 disposed in the cylinder 11. The internal pressure is changed by moving the piston 12 using a motor 13.

The movement control portion 8 is provided for controlling the movement of the pipet portion 9 both horizontally and vertically. FIG. 1 shows a motor 14 which is used to move the piper 9 up and down (viz., vertically).

Encoders 15 and 16 for detecting rotation are provided on the motors 13 and 14, respectively, and their detection signals are sent to the control portion 5.

The numeral 17 designates a pressure sensor provided for measuring the pressure within the cylinder 11. Detection signals from this sensor are sent to the correction calculation portion 4 and the control portion 5.

The numeral 18 designates a sensor which detects splashes of liquid and which is provided for monitoring contamination of the cylinder 11 by the liquid. The reason for this monitoring is that attention must be paid in order to avoid mixing of liquids such as blood and the like during pipetting. Accordingly, it is necessary not only to replace the tip portion for each liquid to be inspected but also to always confirm that no liquid from a previous sample remains in the tip portion. Detection signals from the splash detecting sensor 18 are sent to the control portion 5.

The numeral 19 designates a container which contains a liquid 20.

In the pipetting device 1, the end of the tip portion 10 is first dipped into the liquid 20 in the container 19 by way of positioning control performed by the movement control portion 5 and a negative pressure is produced inside the tip portion 10 by the pressurization/pressure reduction control portion 7 to induct same of the liquid 20.

Specifically, a control target value for induction of the liquid 20 is sent to the correction calculation portion 4 which performs correction calculation based on information from the atmospheric pressure measurement portion 3, the result of the calculation being sent to the control portion 5.

The control portion 5 exerts pressure control over the pressurization/pressure reduction control portion 7 so that the quantity of the liquid 20 inducted equals a specified quantity. Specifically, the distance traveled by the piston 12 (viz., piston displacement) is controlled by the motor 13 which functions as a driving means therefor.

In a memory portion of the control portion 5, data pertaining to the shapes of the cylinder 11, tip portion 10, and the container 19 are stored in advance to allow pressure control to follow up fluctuations in the level of the liquid based on such information along information detected by the pressure sensor 17.

Thereafter, the control portion 5 transfers the tip portion 10 to another container through the movement control portion 8 and causes the pressurization/pressure reduction control portion 7 to pressurize the interior of the tip portion 10. This causes a part of the liquid 20 which has been inducted into the tip portion 10 to be discharged.

Specifically, a control target value for discharge of the liquid 20 is sent to the correction calculation portion 4 which performs correction calculation based on information from the atmospheric pressure measurement portion 3. The result of the calculation is sent to the control portion 5 which in turn controls the distance traveled by the piston 12 using the motor 13, so that the quantity of the liquid 20 discharged exactly equals a specified quantity.

Figure 2:
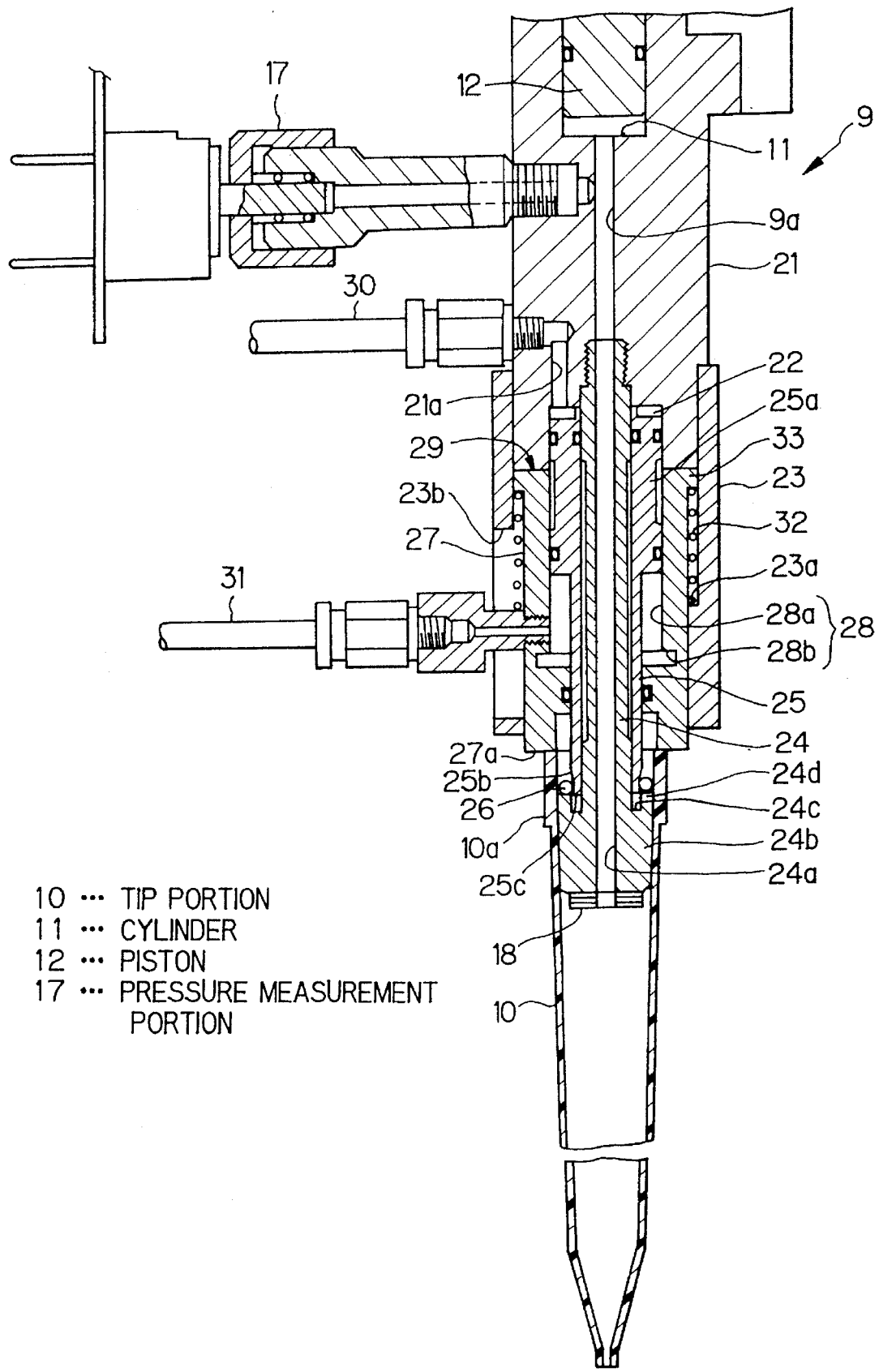
FIG. 2 is a longitudinal sectional view showing major parts of a piper portion of the pipetting device.

FIG. 2 shows a specific example of the configuration of the piper portion 9.

The numeral 21 designates a main portion of the piper portion 9 which is formed of metal. The cylinder 11 is formed in this main portion 21.

A recess 22 is formed at the lower end face of the main portion 21, while an upper end portion of a cylindrical portion 23 is externally secured to a lower part of the main portion 21.

The inner surface of the cylindrical portion 23 is stepped (viz., has different diameter portions) to form an upwardly facing step surface 23a.

A tip shaft 24 which is made of metal comprises a tubular member which has a through bore 24a and which is secured to the main portion 21 at a portion near the upper end thereof.

A portion 24a near the lower end of the tip shaft 24 is made larger in diameter than other portions, and the tip portion 10 is fitted onto this portion. A circular recess 24c which faces upward and a projecting wall 24d which surrounds the recess, are formed at the upper end of the fitted portion 24b.

The through bore 24a in the tip shaft 24 is in communication with the cylinder 11 through the communicating bore 9a formed in the main portion 21.

The tip portion 10 is formed of synthetic resin and is shaped in the form of a tube. The tip portion 10 is made larger in outer diameter at a portion 10a near the upper end thereof compared to other portions which are fitted to the fitted portion 24b of the tip shaft 24. The lower end portion 10b of the tip portion 10 is tapered and is dipped in the liquid 20.

The numeral 25 designates a metallic tubular member having an enlarged diameter which is slidably externally fitted to the tip shaft 24.

The enlarged diameter member 25 has a portion 25a near the upper end thereof which has an outer diameter larger than those of other portions. The upper end portion of the portion 25a is slidably received in the recess 22 of the piper portion 9.

Further, a portion of the enlarged diameter member 25 near the lower end thereof has an outer diameter which becomes smaller toward the lower end to form a tapered portion 25b, and lower end portion 25c thereof has a small and constant outer diameter.

The numeral 26 designates an O-ring which is disposed between the inner wall of the upper end portion 10a of the tip portion 10 and the portion of the enlarged diameter member 25 near the lower end thereof. The projecting wall 24d of the tip shaft 24 serves as a stopper to stop downward movement of the O-ring 26 as a result of downward movement of the enlarged diameter member 25.

The numeral 27 designates a metallic cylindrical tip removing member which is slidably disposed between the enlarged diameter member 25 and the cylindrical portion 23.

The tip removing member 27 is used to remove the upper end portion 10a of the tip portion 10 from the tip shaft 24 by causing a lower end face 27a thereof to abut the upper end portion 10a of the tip portion 10.

The tip removing member 27 is formed with a recess 28 at the upper end thereof for receiving the larger diameter portion 25a of the enlarged diameter member 25. The inner diameter of a portion 28 of the recess excluding the lower end portion thereof, is substantially equal to the outer diameter of the larger diameter portion 25a of the enlarged diameter member 25, and the inner diameter of a lower end portion 28b is greater than the same.

An air cylinder 29 comprises a space defined by the recess 28 and the recess 22 in the main portion 21 serving as a cylinder and the larger diameter portion 25a of the enlarged diameter member 25 serving as a piston.

Specifically, an air pipe 30 for mounting the tip portion 10 is attached to a side of the main portion 21 and is in communication with the recess 22 through a hole 21a formed in the main portion 21.

Further, an air pipe 31 for removing the tip portion 10 is provided, an end of which is secured to a side of the tip removing member 27 through a slot 23b formed on a side of the cylindrical portion 23 to provide communication between the air pipe 31 and the recess 28 in the tip removing member 28.

Therefore, if air pressure control is performed through the air pipes 30 and 31 to increase the pressure inside the recess 22, the enlarged diameter member 25 is lowered. Conversely, if the pressure inside the recess 28 is reduced, the enlarged diameter member 25 is elevated.

The tip removing member 27 is lowered through air pressure control via the air pipe 31.

In summary, the tip removing member 27 is forced down by continuing pressurization in the recess 28 through the air pipe 31 even after the enlarged diameter member 25 reaches the top dead point thereof.

A coil spring 32 (which abuts the lower surface of a flange portion 33 formed at the upper end of the tip removing member 27 at the upper end thereof and abuts the step surface 23a formed inside the cylindrical portion 23 at the lower end thereof) is interposed in a gap formed between the outer circumferential surface of the tip removing member 27 and the cylindrical portion 23. The tip removing member 27 is lowered against an upward bias exerted by the coil spring 32.

Therefore, if the pressure inside the recess 28 is reduced, the tip removing portion 27 is pushed back upward by the elastic force of the coil spring 32.

The slot 23b in the cylindrical portion 23 is formed so as not to hinder the movement of the air pipe 31 as a result of the movement of the tip removing member 27.

The pressure sensor 17 is mounted to a side of the main portion 21 and its detecting end is connected to the communicating hole 9a.

The splash detecting sensor 18 is mounted to the lower end face of the tip shaft 24 to detect whether there is a splash of the liquid or not by the use of a phenomenon wherein any liquid 20 adherent to a fine electrode pattern results in a change in the electrical resistance thereof.

The correction calculation for the atmospheric pressure and the internal pressure of the cylinder 11 will now be described.

Figure 3:
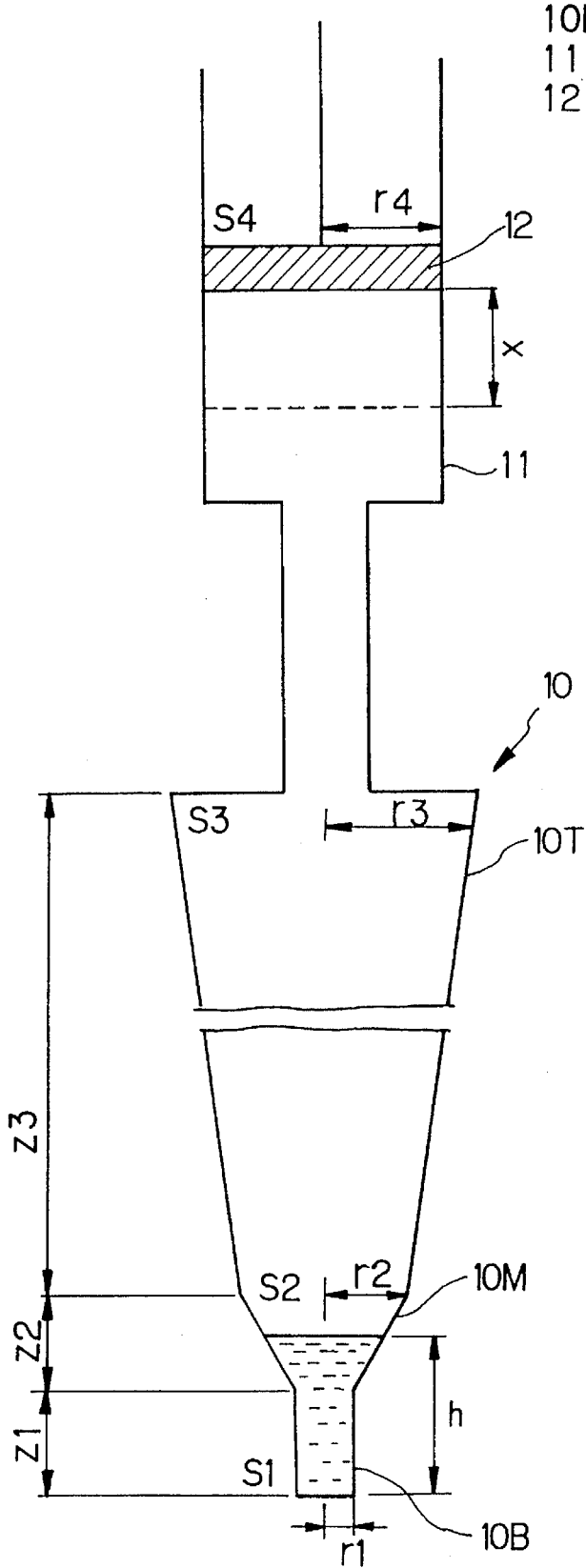
FIG. 3 is a schematic view demonstrating the parameters used in a pressure correction calculation formula used in accordance with the present invention.

FIG. 3 is a schematic view showing the shapes of the tip portion 10 and the cylinder 11 and definitions for quantities contained in the inner diameter of the tip portion 10.

The tip portion 10 is constituted by a bottom portion 10B, a middle portion 10M, and an top portion 10T.

The bottom portion 10B is in the form of a cylinder having an inner radius r1 (cross-sectional area is S1). The middle portion 10M is in the form of an inverted truncated cone having a bottom surface radius r1 and a top surface radius r2 (cross-sectional area is S2). The top portion 10T is in the form of an inverted truncated cone having a bottom surface radius r2 and a top surface radius r2 (cross-sectional area is S3).

The heights of the bottom portion 10B, middle portion 10M, and top portion 10T are z1, z2, and z3, respectively.

The cylinder 11 is in the form of a cylinder having an inner radius r4 and a cross-sectional area S4.

If the atmospheric pressure, the volume of the tip portion 10, the stroke of the piston 12, and the quantity of the liquid 20 inducted are represented by PO, VO, x, and Q, respectively, the value of x can be obtained from relational expressions which are satisfied respectively for the bottom portion 10B, middle portion 10M, and the top portion 10T.

The following table shows the definitions for the reference symbols.

| Symbols | Definition |
| --- | --- |
| r1 | inner radius of bottom portion |
| r2 | inner radius of middle portion |
| r3 | inner radius of top portion |
| r4 | inner radius of cylinder |
| z1 | height of bottom portion |
| z2 | height of middle portion |
| z3 | height of top portion |
| V0 | volume of tip portion |
| Q | quantity inducted at bottom portion |
| S1 | cross-sectional area of bottom portion |
| S2 | cross-sectional area of middle portion |
| S3 | cross-sectional area of top portion |
| S4 | cross-sectional area of cylinder |
| PO | atmospheric pressure |
| X | stoke of piston |

For simplicity, the following description will be made on the assumption that the density of the liquid 20 is 1 and will address three cases, i.e., (1) the period until the bottom portion 10B becomes full, (2) the period until the middle portion 10M becomes full, and (3) the period until the top portion 10T becomes full:

(1) The period until the bottom portion 10B becomes full:

If the height of the inducted liquid measured from the lower end face of the tip portion 10 is represented by h, the relationship expressed by Formula 1 is satisfied according to the Boyle's law and a formula or equation related to the sum of capacities where $0<h<z1$.

$$S4 \cdot x = Q + PO/PO - h1(Q) \cdot VO - VO \ldots \quad \text{Formula 1}$$

where h1(Q)=Q/S1. "h1(Q)" in the above formula represents the elevation head.

According to Formula 1, the stroke x of the piston 12 for a given quantity of induction Q can be calculated if the atmospheric pressure P0 and the shape data S1, S4, and V0 are known.

(2) The period until the middle portion 10M becomes full:

The relationship expressed by Formula 2 is satisfied when z1<h<z2 if the stroke x when the bottom portion 10B is full, is represented by x1; the volume of the air in the tip portion 10 is represented by V1; the internal pressure is represented by P1; the volume of the inducted liquid is represented by Q1; an increase x' in the stroke relative to this state is defined as "x'=x−x1"; and an increase Q' in the volume of the inducted liquid is defined as "Q'=Q−Q1" (Table 2 shows the definitions for the reference symbols).

TABLE 2

| Symbols | Definitions |
| --- | --- |
| x1 | stroke of piston when bottom portion is full; |
| V1 | volume of air in tip portion when bottom portion is full; |
| P1 | internal pressure of tip portion when bottom portion is full; |
| Q1 | volume of inducted liquid when bottom portion is full; |
| x' | increase in stroke of piston in middle portion; |
| Q' | increase in quantity of induction in middle portion. |

$$S4x' = Q' + P1/P1 - h2\,(Q') \cdot V1 - V1 \ldots \quad \text{Formula 2}$$

where $h2\,(Q') = z2/r2 - r1\,(\sqrt[3]{r2 - r1/z2 \cdot 3 \cdot Q'/\pi + (r1)^3} - r1)$ "h2(Q')" in the above formula represents the elevation head.

According to Formula 2, an increase x' in the stroke of the piston 12 for a given increase Q' in the quantity of induction can be calculated if the internal pressure P1 and the shape data S4, V1, r1, r2, and z2 are known.

(3) The period until the middle portion 10M becomes full:

The relationship expressed by Formula 3 is satisfied when z2<h2≦z3 if the stroke x when the middle portion 10M is full, is represented by x2; the volume of the air in the tip portion 10 is represented by V2; the internal pressure is represented by P2; the volume of the inducted liquid is represented by Q2; an increase x" in the stroke relative to this state is defined as "x"=x−x2"; and an increase Q" in the volume of the inducted liquid is defined as "Q"=Q−Q2" (Table 3 shows the definitions for the reference symbols).

TABLE 3

| Symbols | Definitions |
| --- | --- |
| x2 | stroke of piston when middle portion is full; |
| V2 | volume of air in tip portion when middle portion is full; |
| P2 | internal pressure of tip portion when middle portion is full; |
| Q2 | volume of inducted liquid when middle portion is full; |
| x" | increase in stroke of piston in top portion; |
| Q" | increase in quantity of induction in top portion. |

$$S4 \cdot x'' = Q'' + P2/P1 - h3\,(Q'') \cdot V2 - V2 \ldots \quad \text{Formula 3}$$

where $h3(Q'') = z3/r3 - r2 \quad (\sqrt[3]{r3 - r2/z3 \cdot 3 \cdot Q''/\pi + (r2)^3} - r2)$ "h3(Q")" in the above formula represents the elevation head.

According to Formula 3, an increase x" in the stroke of the piston 12 for a given increase Q" in the quantity of induction can be calculated if the internal pressure P2 and the shape data S4, V2, r2, r3, and z3 are known.

As previously described, information on the atmospheric pressure P0 is obtained by the atmospheric pressure measurement portion 3; the internal pressure P1 or P2 is obtained by the pressure sensor 17; and the various shape data are stored in the correction calculation portion 4 in advance. It is therefore possible to calculate the stroke of the piston 12 after correction of the pressure in response to the inducted quantity using Formula 1, 2 or 3.

Needless to say, Formulas 1, 2 and 3 may be used for discharge of the liquid.

The steps of the control performed by the pressurization/pressure reduction control portion 7 including the correction of the atmospheric and internal pressures can be summarized as follows.

(1) A control target value for induction or discharge of a liquid is issued by the command portion 2 to the correction calculation portion 4.

(2) The atmospheric pressure (P0) is measured by the atmospheric pressure measurement portion 3.

(3) The internal pressure (P1 or P2) is measured by the pressure sensor 17.

(4) The correction calculation portion 4 calculates the stroke to be traveled by the piston 12 based on the data obtained in steps (2) and (3) and data on the shapes of the cylinder 11 and the tip portion 10 to satisfy the control target value for induction or discharge of the liquid.

(5) The control portion 5 sends a control signal to the motor 13 to control it so that the stroke of the piston 12 equals the value obtained in step (4).

The order of the measurements at steps (2) and (3) may be reversed. While the measurement of the internal pressure at step (3) is required each time the liquid is inducted or discharged, the measurement of the atmospheric pressure at step (2) is not required so frequently and, therefore, may be performed at predetermined intervals or may be performed by the pressure sensor 17 before induction of the liquid.

Since induction or discharge of a liquid can be performed in a short period of time according to the present embodiment, changes in the ambient temperature are not considered in Formulas 1 through 3. However, influence of changes in the temperature must be considered where induction or discharge of a liquid takes time.

The operation of the pipetting device 1 will now be described separately for induction and discharge of a liquid.

To induct a liquid, a new tip portion 10 is first amounted to the device.

Figure 4:
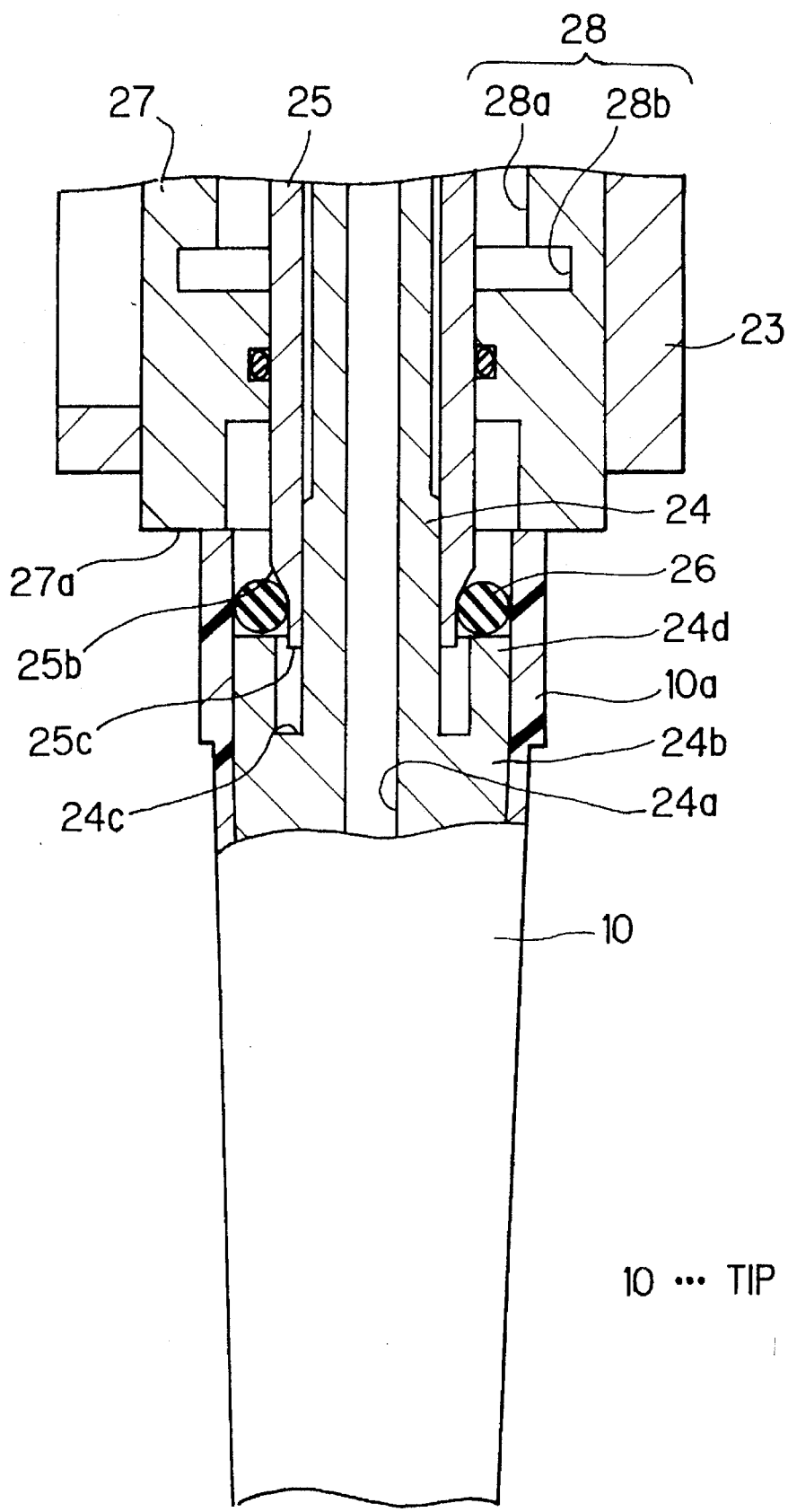
FIG. 4 is an enlarged sectional view of major parts of a tip portion and illustrating the situation wherein an enlarged diameter member of the tip portion has not been lowered.

FIG. 4 shows a state wherein the tip portion 10 is fitted to the tip shaft 24. An upper end portion 10a of the tip portion 10 is externally fitted to the fitted portion 24b of the tip shaft 24, and the enlarged diameter member 25 and the tip removing member 27 are in the highest positions within the ranges of movement permitted.

The O-ring 26 lightly abuts the inner wall of the upper end portion 10a of the tip portion 10 in a dimensional relationship such that the O-ring 26 does not resist the fitting of the tip portion 10 to the fitted portion 24b.

Figure 5:
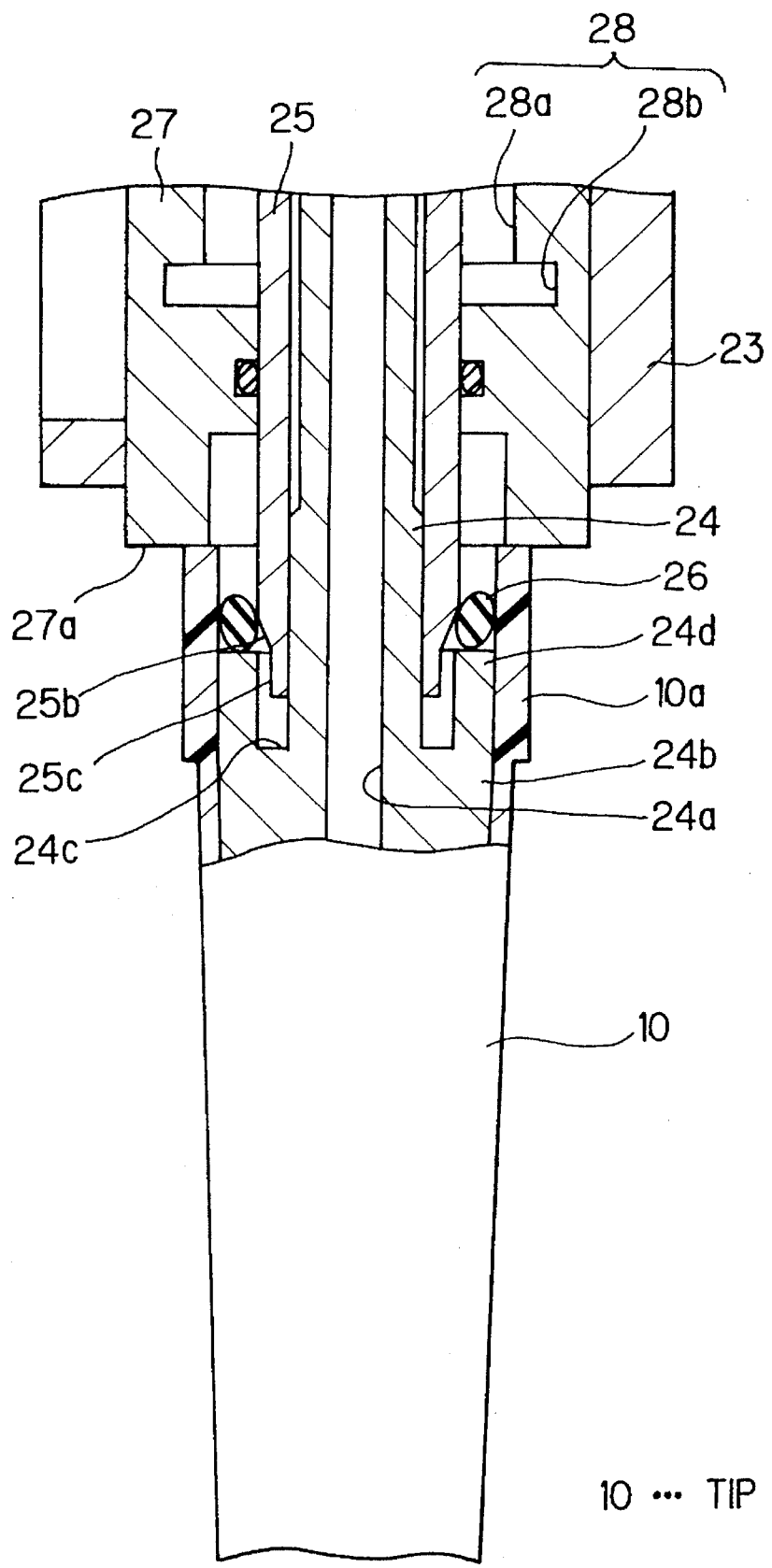
FIG. 5 is an enlarged sectional view of major parts of the tip portion showing the enlarged diameter member in a lowered position.

Pressurization of the interior of the recess 22 through the air pipe 30 lowers the enlarged diameter member 25, thereby causing the inner diameter of the O-ring 26 to be expanded by the tapered portion 25b of the enlarged diameter member 25 as shown in FIG. 5. As a result, the O-ring 26 is compressed between the tapered portion 25b and the upper end portion 10a of the tip portion 10.

Figure 6:
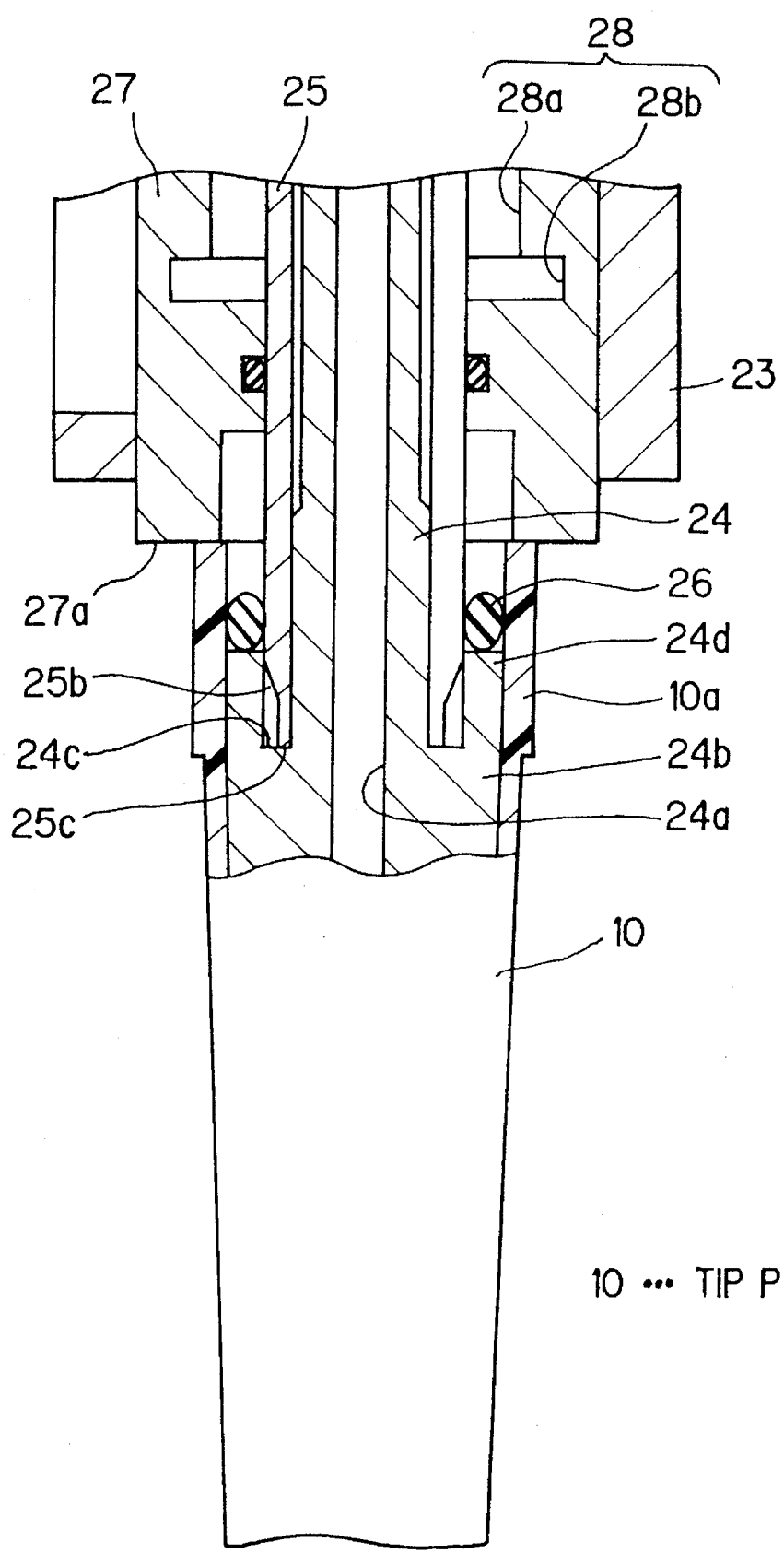
FIG. 6 is an enlarged sectional view of major parts of the tip portion which shows the enlarged diameter member in its lowered condition.

FIG. 6 shows a state wherein the enlarged diameter portion 25 has been lowered further into abutment with the inner bottom surface of the recess 24c of the tip shaft 24 at the lower end portion 25c thereof. In this state, the O-ring 26 extends beyond the tapered portion 25b of the enlarged diameter member 25 to be maximally compressed between a portion slightly higher than the tapered portion 25b and the inner wall of the upper end portion 10a of the tip portion 10.

This provides reliable sealing between the tip portion 10 and the fitted portion 24b of the tip shaft 24. As a result, when the pressure inside the tip portion 10 is reduced to induct the liquid or the interior of the tip portion 10 is pressurized to discharge the liquid thereafter, it is possible to prevent air from leaking in and out through the gap between the tip portion 10 and the fitted portion 24b of the tip shaft 24.

In other words, since the quantity of the liquid inducted or discharged is controlled by controlling the pressure, accurate measurement can be performed with the influence of pressure changes due to air leakage suppressed as much as possible.

After the tip portion 10 is mounted to the device, the piper portion 9 is moved by the movement control portion 8 to put the tip portion 10 on standby above the container 19.

The piper portion 9 is then lowered under control performed by the motor 14 to place the tip portion 10 in the container 19. At this time, the control portion 5 monitors the internal pressure of the tip portion 10 using the pressure sensor 17 and stops the lowering of the piper portion 9 when it is detected that the tip portion 10 has reached the surface of the liquid.

In this state, the lower end portion 10b of the tip portion 10 has been dipped to a position several millimeters below the surface of the liquid.

A correction calculation according to the above-described Formula, 1, 2, or 3 is made based on a control target value from the command portion 2 and information from the atmospheric pressure measurement portion 3 and the pressure sensor 17, and the control portion 5 controls the motor 13 so that the piston 12 will be moved by the stroke obtained by the calculation. This causes a specified quantity of liquid to be inducted into the tip portion 10.

If the pipet portion 9 is in a condition wherein it does not move downward during induction of the liquid, the surface of the liquid inside the container 19 is lowered as induction proceeds. As a result, induction of the liquid is disabled when the lower end portion 10b of the tip portion 10 is in a position above the surface of the liquid.

To prevent this, the control portion 5 calculates the quantity of the drop of the liquid surface based on the quantity of the liquid inducted into the tip portion 10 (the control portion 5 stores data on the shapes of the container 10 and the tip portion 10 required for the calculation of the drop of the liquid surface inside the container 19 relative to the quantity inducted), and controls the motor 13 so that the pipet portion 9 is lowered to follow up the drop of the liquid surface.

This makes it possible to always maintain the lower end portion 10b of the tip portion 10 in a predetermined position slightly below the surface of the liquid.

The purpose of keeping the lower end portion 10b of the tip portion 10 dipped in the vicinity of the surface of liquid is to always induct the supernatant liquid thereby suppressing induction of impurities as much as possible and consequently preventing clogging at the tip portion 10, to prevent the liquid from being unwantedly present on the outer circumferential surface, and to make the conditions for the measurement of the internal pressure of the tip portion 10 constant in order to reduce measurement errors.

After a specified quantity of liquid is inducted, the piper portion 9 is lifted up from the container 19 by the movement control portion 8 to terminate induction.

Next, to discharge the liquid in the tip portion 9, the movement control portion 8 first moves the pipet portion 9 to set the tip portion 10 on standby above a vacant container.

The pipet portion 9 is then lowered under control by the motor 14 to insert the tip portion 10 in the container.

The lower end portion 10b of the tip portion 10 will eventually abut the inner bottom surface of the container. In order to detect this, a sensor (not shown) is provided, and the lowering of the tip portion 10 is stopped in response to a detection signal from this sensor.

The movement control portion 8 slightly lifts up the piper portion 9 and performs control to position the lower end portion 10b of the tip portion 10 at an elevation such that it is kept away from the inner bottom surface of the container with a very small gap therebetween.

Thereafter, the control portion 5 controls the motor 13 so that the stroke of the piston 12 equals a quantity specified by the correction calculation portion 4.

Needless to say, a correction calculation according to the above-described Formula 1, 2, or 3 is made based on a control target value from the command portion 2 and information from the atmospheric pressure measurement portion 3 and the pressure sensor 17, and the control portion 5 controls the motor 13 so that the piston 12 will be moved by the stroke obtained by the calculation.

As a result, the liquid in the tip portion 10 is discharged into the container in a predetermined quantity.

Since the surface of the liquid elevates as discharge proceeds, the tip portion 10 must be elevated to follow up this. Therefore, the control portion 5 controls the height of the piper portion 9 through the movement control portion 8 so that the lower end portion 10b of the tip portion 10 is always kept in a position several millimeters below the surface of the liquid.

The reason is that, in addition to those described above, if the liquid is discharged from the tip portion 10 when the tip portion 10 is not dipped in the liquid, the quantity of a single droplet of the liquid may constitute the limit for the accuracy of the quantity discharged, which situation must be avoided.

After the liquid is discharged in a specified quantity, the pipet portion 9 is lifted up from the container by the movement control portion 8, and the operation of discharging the specified quantity of liquid is repeated for other vacant containers.

When the tip portion 10 is removed after the series of discharging operations as described above are completed, the interior of the recess 28 of the tip removing member 27 is pressurized through the air pipe 31 to elevate the enlarged diameter member 25. Then, changes in the state will take place as shown in FIG. 6, FIG. 5 and FIG. 4 in this order which is the reverse of that for mounting of the tip portion 10.

Figure 7:
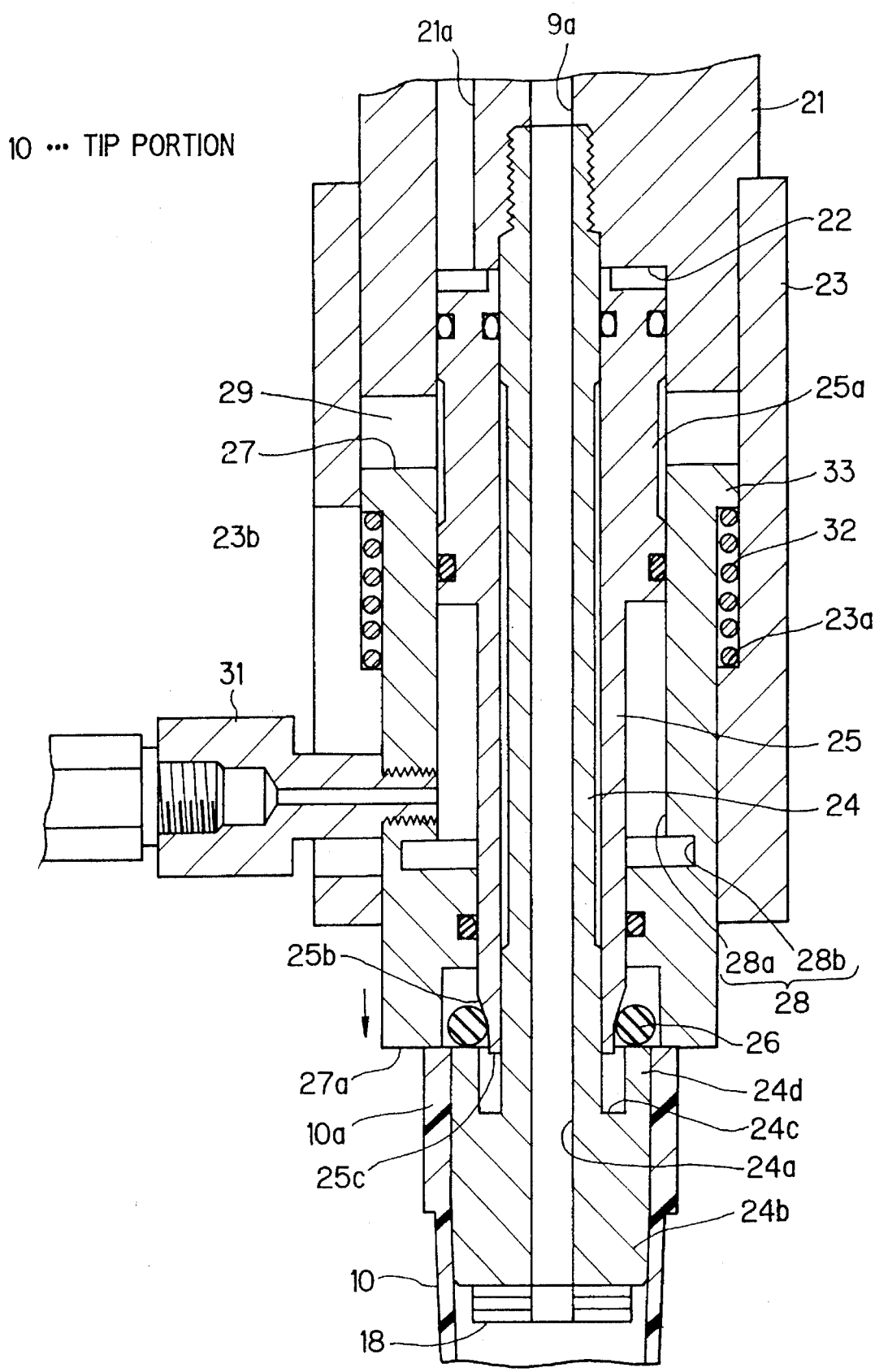
FIG. 7 is an enlarged view showing the removal of the tip portion.

Specifically, if the interior of the recess 28 is further pressurized even after the enlarged diameter member 25 reaches its top dead point, the tip removing member 26 is lowered against the force of the coil spring 32 as shown in FIG. 7, the lower end face 27a thereof causing the tip portion 10 to project downward.

The transformation of the O-ring 26 by the enlarged diameter member 25 has already been canceled and the tip portion 10 is lightly externally fitted to the fitted portion 24b of the tip shaft 24, so the lowering of the tip removing member 27 allows the tip porion 10 to be easily removed.

Thereafter, if the pressure inside the recess 28 of the tip removing member 27 is reduced through the air pipe 31, the tip removing member 27 is elevated by the elastic force of the tip removing member 27 to finally reach the highest position it can take.

During the above-described operations, various kinds of error detection are performed by the control portion 5. For example, the control portion 5 monitors whether the internal pressure of the cylinder 11 is stable or not in periods such as between the termination of liquid induction and the beginning of discharge of the liquid based on information from the pressure sensor 17 to determine leakage of air and the like from a reduction in the internal pressure.

The information on the internal pressure of the cylinder 11 is used to determine whether clogging of the tip portion 10 has occurred during induction of the liquid or whether induction of the liquid is in a proper state (i.e. whether air is being inducted together with the liquid during induction of the liquid).

Figure 8:
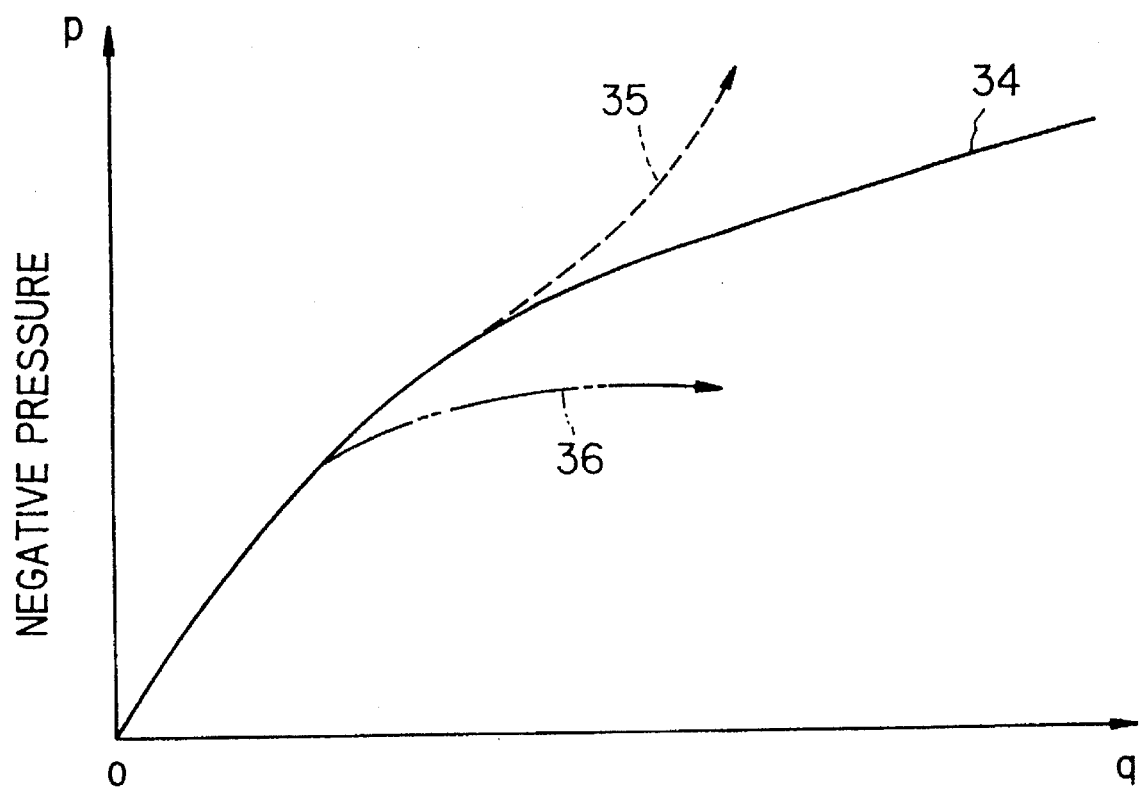
FIG. 8 is a schematic graph depicting error detection based on the detection of an internal pressure.

FIG. 8 indicates the quantity q of the liquid inducted along the axis of abscissa and the internal pressure p (negative pressure) of the cylinder 11 along the axis of ordinate to conceptually illustrate the relationship therebetween.

The curve 34 in a solid line indicates a normal state of induction. The curve 35 in a dotted line indicates a change in the state which occurs when the tip portion 10 is clogged. The curve 36 in a chain double-dashed line indicates a change in the state which occurs when air is inducted together with the liquid.

Clogging of the tip portion 10 with impurities included in the liquid increases resistance during induction, which results in an abnormal reduction in the internal pressure p relative to the quantity inducted q as indicated by the curve 35.

Conversely, when air is inducted together with the liquid, the internal pressure p exhibits an abnormal increase relative to the quantity inducted q as indicated by the curve 36.

Abnormality in the state of induction can be detected by continuously monitoring such changes in the pressure based on the information from the pressure sensor 17.

As apparent from the above, the device and method for inducting and discharging liquid make it possible to reduce measurement errors due to fluctuations in the atmospheric pressure changes in the internal pressure of the tip portion by performing pressure correction calculation based on data measured on the internal pressure of the cylinder and data on the shape of the cylinder portion to obtain the distance to be traveled by the piston taking the changes in the pressure into consideration.

In performing pressure correction calculation, the cylinder portion and tip portion may be divided into a plurality of parts each of which has a constant rate of change for the inner diameter thereof, and the distance traveled by the piston may be obtained for each part according to the correction calculation formula corresponding to that part. This allows precise pressure control taking shape factors associated with the cylinder portion and tip portion into consideration, thereby assuring highly accurate measurement.

The shapes and structures described in the above embodiment are merely examples for implementation of the present invention and should not be taken as limiting the technical scope of the present invention.

For example, the present invention is applied to a pipetting device having a configuration wherein a tip portion may be replaced in the above-described embodiment. It goes without saying, however, that various modes of implementation such as application of the present invention to a pipetting device of a type wherein a tip portion can not be replaced fall within the technical scope of the present invention as long as they do not depart from the teachings of the present invention.

What is claimed is:

1. A pipetting device for inducting or discharging a specified quantity of liquid by controlling the pressure in a cylinder-like portion, said cylinder-like portion including a cylinder and a piston slidably disposed in the cylinder, comprising:

a command portion for specifying a control target value for a quantity of liquid to be inducted or discharged, a pressure measurement portion for measuring atmospheric pressure and an internal pressure of the cylinder;

a correction calculation portion for calculating a distance to be traveled by the piston by making a calculation to correct the control target value specified by the command portion based on measured data from the pressure measurement portion and data indicative of a shape of a portion of the cylinder-like portion into which liquid is inducted; and a control portion for controlling a piston driving means according to the distance to be traveled by the piston calculated by the correction calculation portion.

2. A method of pipetting a liquid wherein a specified quantity of liquid is inducted or discharged by controlling the pressure in a cylinder-like portion, said cylinder-like portion including a piston and a cylinder in which the piston is reciprocatively received, comprising the steps of:

specifying a control target value for the quantity of the liquid to be inducted or discharged;

measuring an atmospheric pressure and an internal pressure of the cylinder;

obtaining the distance to be traveled by the piston by making a calculation to correct the control target value based on the measured atmospheric and internal pressure of the cylinder and data indicative of a shape of a tip portion of the cylinder-like portion; and controlling the travel of the piston in the cylinder so that the distance traveled by the piston equals the value obtained by the correction calculation.

3. The pipetting device according to claim 1, wherein said portion of said cylinder-like portion into which liquid is inducted comprises:

a tip portion which is in communication with the cylinder, and which is detachably mounted on a part of the cylinder-like portion in which the cylinder is formed, said tip portion receiving the liquid which is inducted; and wherein said pipetting device further comprises:

pressurized air responsive means for mounting and removing said tip portion from the part of the cylinder-like portion in which said cylinder is formed.

4. A pipetting device for inducting or discharging a specified quantity of liquid by controlling a pressure in a cylinder-like portion, said cylinder-like portion including a piston and a cylinder, said pipetting device comprising:

a command portion for specifying a control target value for a quantity of liquid to be inducted or discharged;

a pressure measurement portion for measuring at least one of an atmospheric pressure and an internal pressure of the cylinder;

a correction calculation portion for calculating a distance to be traveled by the piston by correcting the control target value based on measured data from the pressure measurement portion and data indicative of a shape of a portion of the cylinder-like portion into which liquid is inducted; and a control portion for controlling a piston driving means according to information indicative of the distance to be traveled by the piston calculated by the correction calculation portion;

wherein the portion of the cylinder-like portion into which liquid is inducted comprises a tip portion which is divided into a plurality of parts each of which has a constant rate of change for the inner diameter thereof, and wherein the correction calculation portion calculates the distance to be travelled by the piston for each part of the tip portion according to a correction calculation formula corresponding to each said part of the tip portion.

5. A pipetting device for inducting or discharging a specified quantity of liquid by controlling a pressure in a cylinder-like portion, said cylinder-like portion including a cylinder and a piston reciprocatively disposed in the cylinder, said pipetting device comprising:

a command portion for specifying a control target value for a quantity of liquid to be inducted or discharged;

a pressure measurement portion for measuring at least one of an atmospheric pressure and an internal pressure of the cylinder;

a correction calculation portion for calculating a distance to be traveled by the piston by correcting the control target value based on measured data from the pressure measurement portion and data indicative of a shape of the cylinder-like portion;

a control portion for controlling a piston driving means according to information indicative of the distance to be traveled by the piston calculated by the correction calculation portion; and a tip portion into which liquid is inducted, said tip portion being communicated with the cylinder and detachably mounted on a portion of the cylinder-like portion in which the cylinder is formed;

said tip portion being divided into a plurality of parts each of which has a constant rate of change for the inner diameter thereof, and said correction calculation portion calculating the distance to be traveled by the piston in the cylinder for each corresponding part of the tip portion according to a correction calculation formula corresponding to each part of the tip portion.

6. A pipetting device comprising:

a cylinder in which a piston is reciprocatively disposed;

a tip including a chamber into which liquid is inducted, said chamber having a predetermined shape and being in fluid communication with said cylinder in a manner wherein displacement of the piston within said cylinder varies the pressure in said chamber;

means for measuring atmospheric pressure;

means for measuring a pressure in said cylinder;

a memory in which data indicative of the shape of said chamber is stored; and correction means for determining a piston displacement distance necessary to pipette a predetermined amount of liquid based on:
a) the measured atmospheric pressure,
b) the measured pressure in said cylinder, and
c) the memorized shape of said chamber.

7. A pipetting device according to claim 6, wherein said tip is detachably connected to said pipetting device.

8. A pipetting device according to claim 7, further comprising a pressurized air responsive arrangement for mounting and removing said tip from said pipetting device.

9. A pipetting device according to claim 6, further comprising splash detection means for detecting splashes of liquid in said chamber.

\* \* \* \* \*